(12) United States Patent
Kassab et al.

(10) Patent No.: US 9,907,954 B2
(45) Date of Patent: Mar. 6, 2018

(54) DEVICES AND SYSTEMS FOR ACCESSING CARDIAC TISSUE

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 340 days.

(21) Appl. No.: 14/552,708

(22) Filed: Nov. 25, 2014

(65) Prior Publication Data

US 2015/0080805 A1    Mar. 19, 2015
US 2016/0339210 A9    Nov. 24, 2016

Related U.S. Application Data

(63) Continuation of application No. 12/816,655, filed on Jun. 16, 2010, now Pat. No. 8,894,606, which is a (Continued)

(51) Int. Cl.
*A61N 1/05*    (2006.01)
*A61B 17/00*   (2006.01)
(Continued)

(52) U.S. Cl.
CPC ........ *A61N 1/0592* (2013.01); *A61B 17/0057* (2013.01); *A61B 17/00234* (2013.01); *A61B 17/00491* (2013.01); *A61B 17/30* (2013.01); *A61M 5/14* (2013.01); *A61M 25/0084* (2013.01); *A61M 25/04* (2013.01); *A61M 25/0662* (2013.01); *A61B 2017/0065* (2013.01); *A61B 2017/00243* (2013.01); *A61B 2017/00292* (2013.01); *A61B 2017/00575* (2013.01); *A61B 2017/00606* (2013.01); (Continued)

(58) Field of Classification Search
CPC ............... A61M 25/04; A61M 1/0592; A61M 25/0662; A61M 2210/125; A61M 2025/004; A61M 2025/0039; A61N 1/0592; A61B 17/00234; A61B 2017/00243; A61B 2017/306
See application file for complete search history.

(56) References Cited

U.S. PATENT DOCUMENTS 3,583,404 A    6/1971   McWhorter
3,630,207 A    12/1971  Kahn et al.
(Continued)

OTHER PUBLICATIONS

International Searching Authority, International Search Report, PCT/US07/15207, dated Sep. 11, 2008.
(Continued)

*Primary Examiner* — Bradley Osinski
(74) *Attorney, Agent, or Firm* — Reichel Stohry LLP; Mark C. Reichel; Natalie J. Dean (57) ABSTRACT

Devices, systems, and methods for accessing the internal and external tissues of the heart are disclosed. At least some of the embodiments disclosed herein provide access to the external surface of the heart through the pericardial space for localized delivery of substances to the heart tissue. In addition, various disclosed embodiments provide access to the internal surface of the heart for aspiration and delivery of substances to a targeted region without disturbing or interfering with nearby structures or surfaces.

18 Claims, 9 Drawing Sheets

Related U.S. Application Data continuation of application No. 12/305,864, filed as application No. PCT/US2007/015207 on Jun. 29, 2007, now abandoned.

(60) Provisional application No. 60/817,421, filed on Jun. 30, 2006, provisional application No. 60/914,452, filed on Apr. 27, 2007.

(51) Int. Cl.
*A61M 25/00* (2006.01)
*A61M 25/04* (2006.01)
*A61M 25/06* (2006.01)
*A61M 5/14* (2006.01)
*A61B 17/30* (2006.01)

(52) U.S. Cl.
CPC .......... *A61B 2017/306* (2013.01); *A61M 2025/0004* (2013.01); *A61M 2025/0039* (2013.01); *A61M 2210/125* (2013.01)

(56) References Cited

U.S. PATENT DOCUMENTS

| | | | |
|---|---|---|---|
| 4,946,457 A | | 8/1990 | Elliott |
| 4,991,578 A | * | 2/1991 | Cohen .............. A61N 1/0587 607/2 |
| 5,195,968 A | | 3/1993 | Lundquist et al. |
| 5,292,332 A | | 3/1994 | Lee |
| 5,715,817 A | | 2/1998 | Stevens-Wright et al. |
| 5,972,013 A | * | 10/1999 | Schmidt .............. A61B 17/3417 604/164.01 |
| 6,113,611 A | | 9/2000 | Allen et al. |
| 6,200,303 B1 | | 3/2001 | Verrior et al. |
| 6,338,345 B1 | | 1/2002 | Johnson et al. |
| 6,500,167 B1 | | 12/2002 | Webster, Jr. |
| 6,595,982 B2 | | 7/2003 | Sekino et al. |
| 6,613,062 B1 | | 9/2003 | Leckrone et al. |
| 6,626,930 B1 | | 9/2003 | Allen et al. |
| 6,663,633 B1 | | 12/2003 | Pierson, III |
| 6,692,458 B2 | | 2/2004 | Forman et al. |
| 6,776,784 B2 | | 8/2004 | Ginn |
| 6,837,893 B2 | | 1/2005 | Miller |
| 6,890,295 B2 | * | 5/2005 | Michels .............. A61B 17/3415 600/114 |
| 6,918,890 B2 | | 7/2005 | Schmidt |
| 6,991,616 B2 | | 1/2006 | Bencini et al. |
| 7,029,468 B2 | | 4/2006 | Honebrink |
| 7,081,125 B2 | | 7/2006 | Edwards et al. |
| 7,326,231 B2 | | 2/2008 | Philiips et al. |
| 7,842,068 B2 | | 11/2010 | Ginn |
| 7,931,628 B2 | | 4/2011 | Zhu et al. |
| 7,942,897 B2 | | 5/2011 | Lafontaine |
| 2001/0053909 A1 | * | 12/2001 | Nakada .............. A61B 1/00089 606/47 |
| 2002/0072768 A1 | | 6/2002 | Ginn |
| 2002/0091354 A1 | | 7/2002 | Navia et al. |
| 2002/0165561 A1 | | 11/2002 | Ainsworth et al. |
| 2002/0168317 A1 | | 11/2002 | Daighighian et al. |
| 2003/0109852 A1 | | 6/2003 | Peterson et al. |
| 2003/0225420 A1 | | 12/2003 | Wardle |
| 2004/0010216 A1 | | 1/2004 | Zhu et al. |
| 2004/0018228 A1 | | 1/2004 | Fischell et al. |
| 2004/0086479 A1 | | 5/2004 | Grinstaff et al. |
| 2004/0230131 A1 | | 11/2004 | Kassab et al. |
| 2005/0133760 A1 | | 6/2005 | Farrand et al. |
| 2005/0256450 A1 | | 11/2005 | Palasis et al. |
| 2006/0106442 A1 | | 5/2006 | Richardson et al. |
| 2006/0217764 A1 | | 9/2006 | Abbott et al. |

OTHER PUBLICATIONS

International Searching Authority, Written Opinion of the International Searching Authority, PCT/US07/15207, dated Sep. 11, 2008.
Hertzberg, et al, "Sonographic assessment of . . . ", American Journal of Roentgenology, May 1997, vol. 168, No. 5, pp. 1253-1257. Viewable at wwvv.ajronline.org/content/168/5/1253.
Prince, et al., "The diameter of the inferior vena cava . . . ", Radiology, Dec. 1983; 149(3) 687-9. Viewable at www.ncbi.nlm.nih.gov/pubmed/6647844.
Uchida, et al.; "Angiogenic therapy of acute myocardial infarction by intrapericardial injection of . . . ", American Heart Journal, vol. 130, No. 6, pp. 1182-1188 (Dec. 1995).

* cited by examiner

DEVICES AND SYSTEMS FOR ACCESSING CARDIAC TISSUE

PRIORITY

This U.S. continuation patent application is related to, and claims the priority benefit of, U.S. Nonprovisional patent application Ser. No. 12/816,655, filed Jun. 16, 2010 and issued as U.S. Pat. No. 8,894,606 on Nov. 25, 2014, which is related to, claims the priority benefit of, and is a U.S. continuation patent application of, U.S. Nonprovisional patent application Ser. No. 12/305,864, filed Dec. 19, 2008, now abandoned, which is related to, claims the priority benefit of, and is a U.S. national stage application of, International Patent Application No. PCT/US2007/015207, filed Jun. 29, 2007, which is related to, and claims the priority benefit of, U.S. Provisional Patent Application Ser. No. 60/914,452, filed Apr. 27, 2007, and U.S. Provisional Patent Application Ser. No. 60/817,421, filed Jun. 30, 2006. The contents of each of these applications are hereby incorporated by reference in their entirety into this disclosure.

BACKGROUND

Ischemic heart disease, or coronary heart disease, kills more Americans per year than any other single cause. In 2004, one in every five deaths in the United States resulted from ischemic heart disease.

Ischemic heart disease is generally characterized by a diminished flow of blood to the myocardium and is also often treated using drug therapy. Although many of the available drugs may be administered systemically, local drug delivery ("LDD") directly to the heart can result in higher local drug concentrations with fewer systemic side effects, thereby leading to improved therapeutic outcomes.

Cardiac drugs may be delivered locally via catheter passing through the blood vessels to the inside of the heart. However, endoluminal drug delivery has several shortcomings, such as: (1) inconsistent delivery, (2) low efficiency of localization, and (3) relatively rapid washout into the circulation.

To overcome such shortcomings, drugs may be delivered directly into the pericardial space, which surrounds the external surface of the heart. The pericardial space is a cavity formed between the heart and the relatively stiff pericardial sac that encases the heart. Although the pericardial space is usually quite small because the pericardial sac and the heart are in such close contact, a catheter may be used to inject a drug into the pericardial space for local administration to the myocardial and coronary tissues. Drug delivery methods that supply the agent to the heart via the pericardial space offer several advantages over endoluminal delivery, including: (1) enhanced consistency and (2) prolonged exposure of the drug to the cardiac tissue.

In current practice, drugs are delivered into the pericardial space either by the percutaneous transventricular method or by the transthoracic approach. The percutaneous transventricular method involves the controlled penetration of a catheter through the ventricular myocardium to the pericardial space. The transthoracic approach involves accessing the pericardial space from outside the heart using a sheathed needle with a suction tip to grasp the pericardium, pulling it away from the myocardium to enlarge the pericardial space, and injecting the drug into the space with the needle.

Clinically, the only approved non-surgical means for accessing the pericardial space include the subxiphoid and the ultrasound-guided apical and parasternal needle catheter techniques, and each methods involves a transthoracic approach. In the subxiphoid method, a sheathed needle with a suction tip is advanced from a subxiphoid position into the mediastinum under fluoroscopic guidance. The catheter is positioned onto the anterior outer surface of the pericardial sac, and the suction tip is used to grasp the pericardium and pull it away from the heart tissue, thereby creating additional clearance between the pericardial sac and the heart. The additional clearance tends to decrease the likelihood that the myocardium will be inadvertently punctured when the pericardial sac is pierced.

Although this technique works well in the normal heart, there are major limitations in diseased or dilated hearts—the very hearts for which drug delivery is most needed. When the heart is enlarged, the pericardial space is significantly smaller and the risk of puncturing the right ventricle or other cardiac structures is increased. Additionally, because the pericardium is a very stiff membrane, the suction on the pericardium provides little deformation of the pericardium and, therefore, very little clearance of the pericardium from the heart.

Thus, there is need for an efficient, easy to use, and relatively inexpensive technique that can be used to access the heart for local delivery of therapeutic and diagnostic substances.

BRIEF SUMMARY

Various embodiments disclosed herein relate to systems, devices, and methods for accessing specific tissues of the heart and for delivering substances to the cardiac tissue. For example, using certain embodiments, a substance may be delivered to a specifically targeted area of the interior of a wall of the heart (i.e., "targeted tissue"). Certain other embodiments provide for access to the tissue on the external surface of the heart by delivering a substance to the pericardial space using a non-surgical, percutaneous route that is both rapid and safe. Indeed, many of the disclosed embodiments avoid percutaneous subxiphoid puncture and hence the associated increased risk of right ventricular lesions, as well as the anterior thoracotomy for pericardial window procedure.

At least some of the embodiments disclosed herein include a system for accessing the tissue of a heart comprising an engagement catheter having a proximal end, a distal end, and first and second lumens extending between the proximal end and the distal end. A vacuum port is located at the proximal end of the engagement catheter and is operatively connected to the first lumen of the engagement catheter and capable of operative connection to a vacuum source. The first lumen of the engagement catheter includes a suction port located at or near the catheter's distal end, and the suction port is configured to removably attach to a targeted tissue on the interior of a wall of the heart. The wall may be an atrial wall or a wall of the atrial appendage. The suction port is capable of forming a reversible seal with the targeted tissue when the vacuum source is operatively attached to the vacuum port, and the system is capable of enlarging a pericardial space between the targeted tissue and a pericardial sac that surrounds the heart by retracting the targeted tissue away from the pericardial sac.

The system also includes a delivery catheter comprising a proximal end, a distal end, and a hollow tube extending between the proximal end and the distal end, and the delivery catheter may be configured to be inserted into the second lumen of the engagement catheter. A needle may be located at the distal end of the delivery catheter, and the needle may include a pressure tip or a needle wire. In some embodiments, the delivery catheter may include a first lumen for delivering a fluid to the pericardial space. Further, the delivery catheter may be configured to fit within the second lumen of the engagement catheter such that the needle is positioned to be capable of piercing the targeted tissue when the suction port is attached to the targeted tissue, and such that, when the tissue is pierced, access to the pericardial space is achieved.

In various embodiments, the engagement catheter also has, in fluid communication with its second lumen, an injection channel that is configured to administer a fluid to the targeted tissue. The system may include a fluid, such as an adhesive, for administration to the targeted tissue through the injection channel. The injection channel may be formed along the length of the engagement catheter, may have at its distal end at least one opening for administering a fluid to the heart tissue, and may be capable of operable attachment to an external fluid source at the proximal end of the injection channel such that fluid from the external fluid source can flow through the injection channel to the targeted tissue when the external fluid source is operatively attached to the injection channel. In some embodiments, the injection channel is ring-shaped.

Also disclosed herein are embodiments of an engagement catheter to be used with a vacuum source in accessing heart tissue. Such embodiments include an elongated tube comprising a proximal end, a distal end, an outer wall positioned circumferentially along the length of the tube, and an inner wall positioned circumferentially along the length of the tube, wherein the outer wall and the inner wall form at least one suction channel along the length of the tube between the outer wall and the inner wall; a vacuum port in communication with the proximal end of the tube, the vacuum port being operatively connected to the at least one suction channel and capable of operative connection to the vacuum source; and a suction port in communication with the at least one suction channel at the distal end of the tube. The suction port is configured to removably attach to targeted tissue on the interior of a wall of the heart and is capable of forming a reversible seal with the heart wall when the vacuum source is operatively attached to the vacuum port. When the suction port is attached to the targeted tissue, the engagement catheter is capable of enlarging the pericardial space between the heart and the pericardial sac.

Certain embodiments include at least one internal lumen support positioned within the suction channel and attached to the outer wall and the inner wall. Each internal lumen support may extend from the distal end of the tube along at least a substantial portion of the length of the tube. In embodiments having two internal lumen supports, the lumen supports form two suction channels.

At least some of the embodiments of an engagement catheter disclosed herein have an injection channel formed along the length of the tube, the injection channel having at its distal end at least one opening for administering a fluid to the targeted tissue. The injection channel is capable of operable attachment to an external fluid source at the proximal end of the injection channel such that fluid from the external fluid source can flow through the injection channel to the heart tissue when the external fluid source is operatively attached to the injection channel.

Various embodiments disclosed herein include a delivery catheter for use in accessing heart tissue. Some delivery catheter embodiments include an elongated hollow tube comprising a proximal end, a distal end, a lumen, a needle extending from the distal end of the tube, and a security notch formed circumferentially around the needle. The security notch is configured to prevent over-perforation of the needle when piercing a wall of the heart into the pericardial space. The tube of some embodiments of delivery catheter further includes one or more openings for administering a fluid to an external surface of the heart located in the pericardial space, such that the at least one opening is in fluid communication with the lumen of the tube. In at least some embodiments, an elongated guide wire may be placed inside the lumen of the tube and inserted into the pericardial space.

Also disclosed herein are various methods for accessing heart tissue. Certain embodiments include the steps of providing a system as disclosed herein; inserting an engagement catheter into the body such that the distal end of the engagement catheter is positioned inside the heart and the suction port is in contact with the interior of a wall of the heart; operatively connecting a vacuum source to the vacuum port such that the suction port is reversibly attached to a targeted tissue on the interior of a wall of the heart; inserting the delivery catheter into the second lumen of the engagement catheter; piercing the targeted tissue with the needle; and administering a substance into the pericardial space. In some embodiments, the method also includes the step of administering a substance to the targeted tissue after withdrawal of the needle, and the substance may include an adhesive for sealing a puncture wound in the targeted tissue.

Certain other embodiments include the steps of extending into a blood vessel an elongated hollow tube having a proximal end, a distal end, and at least one lumen, such that the distal end of the tube is in contact with the interior of a wall of the heart; aspirating a targeted tissue on the interior of a wall of the heart such that the wall of the heart is retracted away from a pericardial sac surrounding the heart to enlarge a pericardial space between the pericardial sac and the wall of the heart; delivering a fluid onto the targeted tissue; and removing the elongated tube from the body. Such embodiments may further include the steps of inserting through a lumen of the elongated tube a delivery catheter having a proximal end, a distal end, and a needle located at the distal end, such that the needle is located within the heart; inserting the needle into the targeted tissue on the interior of the wall of the heart; and injecting a fluid into the pericardial space such that the fluid contacts the exterior of the heart within the pericardial space. In at least some embodiments, the needle is withdrawn after puncture, and the distal end of a guide wire is inserted through the lumen of the delivery catheter and into the pericardial space. The delivery catheter may then be inserted into the pericardial space.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosed embodiments include devices, systems, and methods useful for accessing various tissues of the heart from inside the heart. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, epicardial pacing leads may be delivered via the pericardial space, and an ablation catheter may be used on the epicardial tissue from the pericardial space.

Figure 1A:
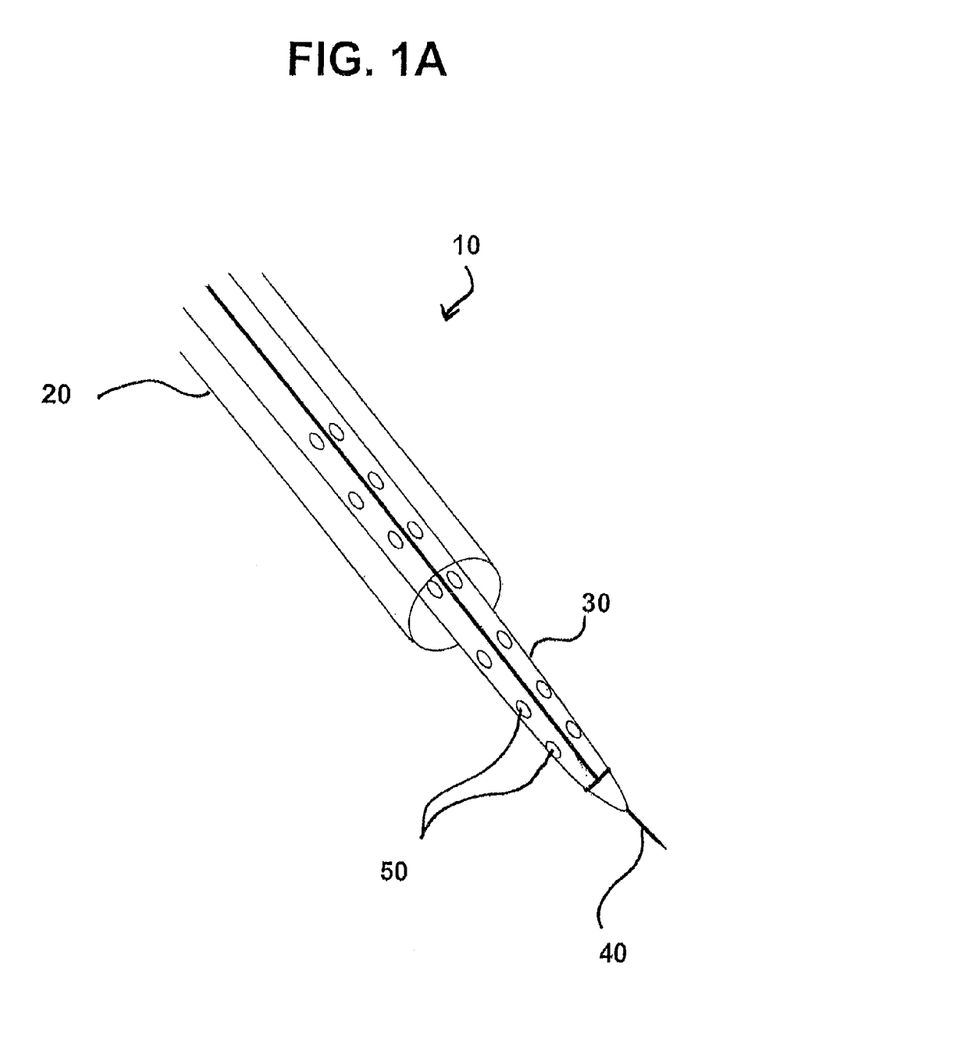
FIG. 1A shows an embodiment of an engagement catheter and an embodiment of a delivery catheter as disclosed herein.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter.

Figure 2A:
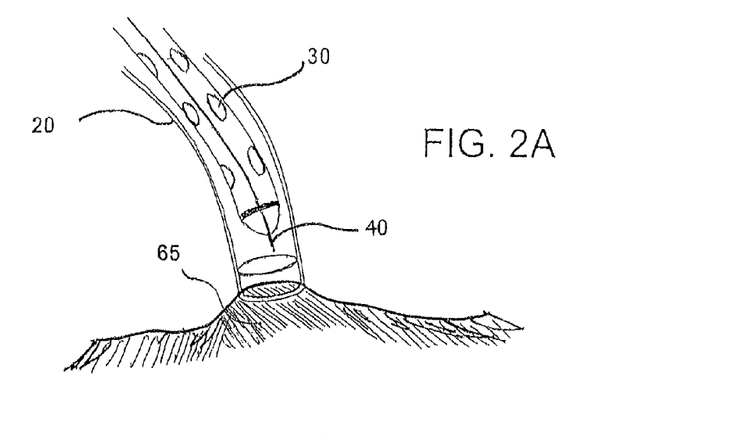
FIG. 2A shows a percutaneous intravascular technique for accessing the pericardial space through a right atrial wall or atrial appendage using the engagement and delivery catheters shown in FIG. 1A.
Figure 2B:
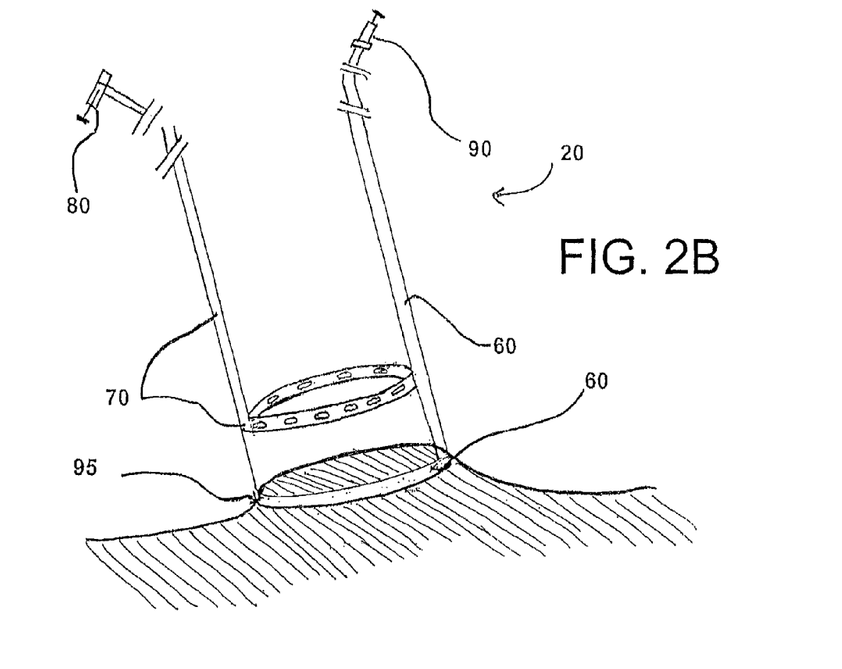
FIG. 2B shows the embodiment of an engagement catheter shown in FIG. 2A.
Figure 2C:
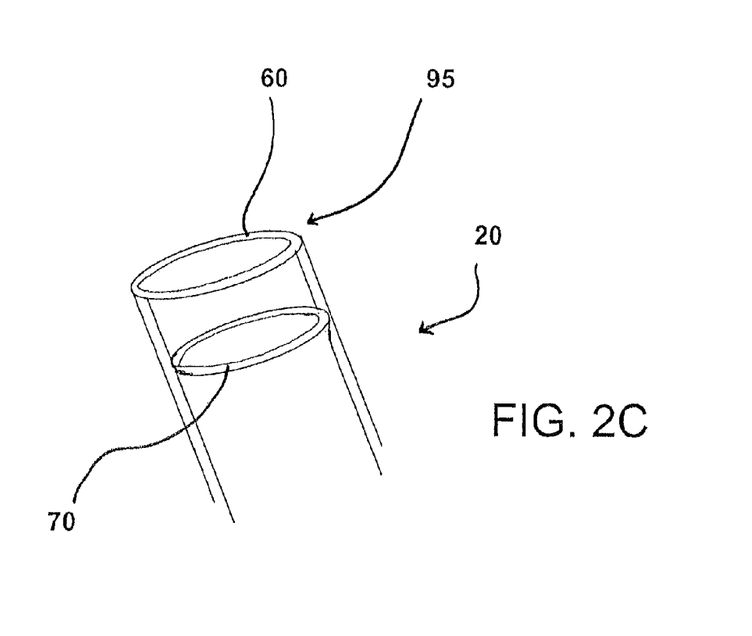
FIG. 2C shows another view of the distal end of the engagement catheter embodiment shown in FIGS. 2A and 2B.

As shown in more detail in FIGS. 2A, 2B, and 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Figure 1B:
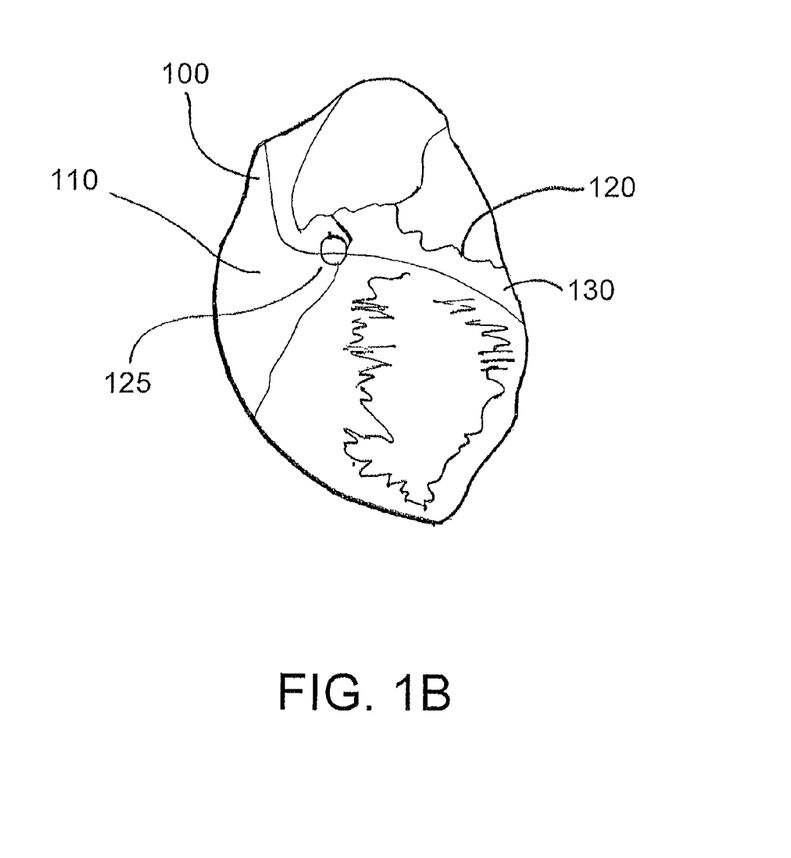
FIG. 1B shows a percutaneous intravascular pericardial delivery using another embodiment of an engagement catheter and another embodiment of a delivery catheter as disclosed herein.

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Fluoroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transeptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Figure 3A:
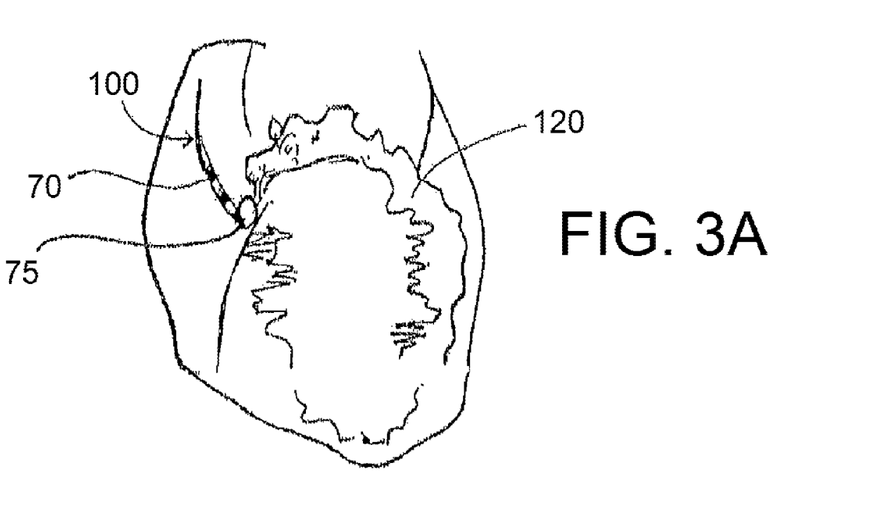
FIG. 3A shows removal of an embodiment of a catheter as disclosed herein.
Figure 3B:
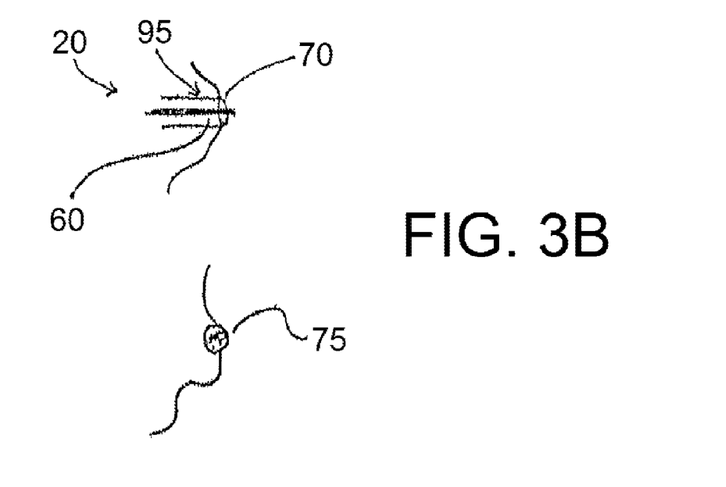
FIG. 3B shows the resealing of a puncture according to an embodiment as disclosed herein.

Referring now to FIG. 3A, the catheter system shown in FIG. 1B is retrieved by pull back through the route of entry. However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity of the heart, as discussed herein; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Figure 4A:
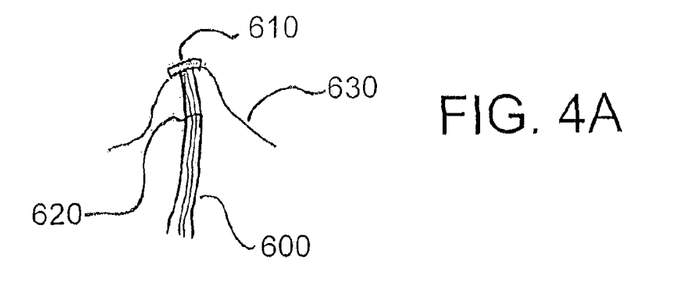
FIG. 4A to 4C show a closure of a hole in the atrial wall using an embodiment as disclosed herein.
Figure 4B:
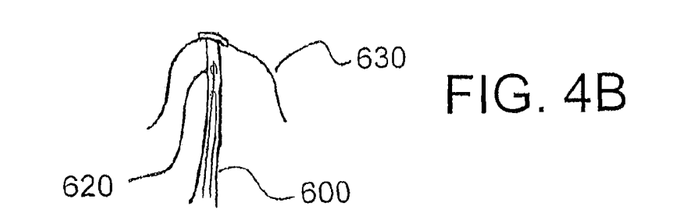
Figure 4C:
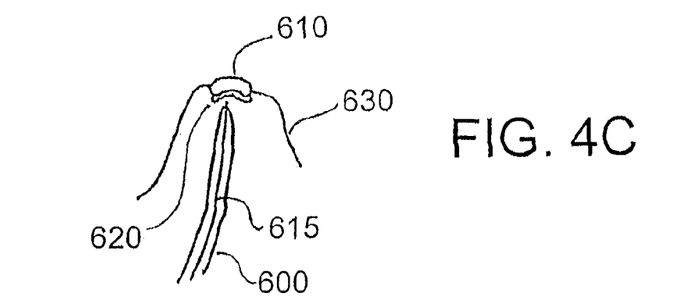

Other examples for sealing the puncture wound in the atrial wall or appendage are shown in FIGS. 4A, 4B, and 4C. A sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded once it is outside of the catheter. As shown in FIG. 4A, external cover 610 is deployed (in its expanded configuration) on the outside of the atrial wall to seal a puncture wound in the targeted tissue. Internal cover 620 is delivered through engagement catheter 600 (in its folded configuration), as shown in FIGS. 4A and 4B. Once internal cover 620 is in position on the inside of atrial wall 630 at the targeted tissue, internal cover 620 is deployed to help seal the puncture wound in the targeted tissue (see FIG. 4C). Engagement catheter 600 then releases its grip on the targeted tissue and is withdrawn, leaving the sandwich-type closure to seal the puncture wound, as shown in FIG. 4C. External cover 610 and internal cover 620 may be held in place using adhesion or magnetic forces.

FIGS. 5A, 5B, 5C, and 5D show another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

Figures 5A, 5B, 5C:
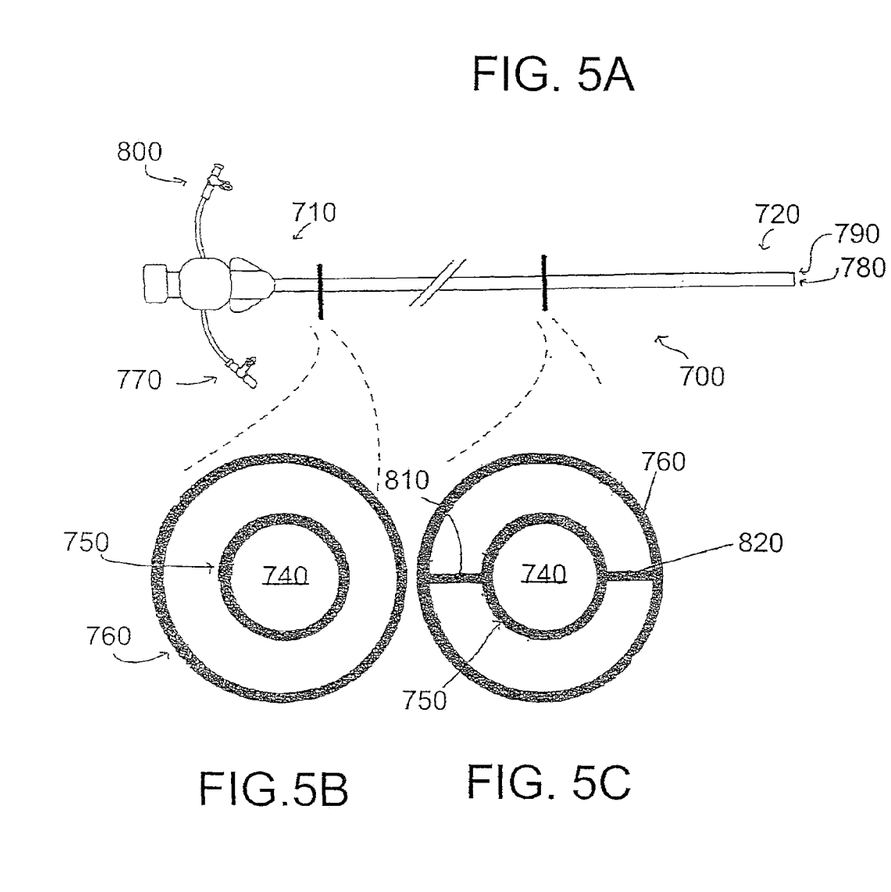
FIG. 5A shows an embodiment of an engagement catheter as disclosed herein.
FIG. 5B shows a cross-sectional view of the proximal end of the engagement catheter shown in FIG. 5A.
FIG. 5C shows a cross-sectional view of the distal end of the engagement catheter shown in FIG. 5A.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

Figure 5D:
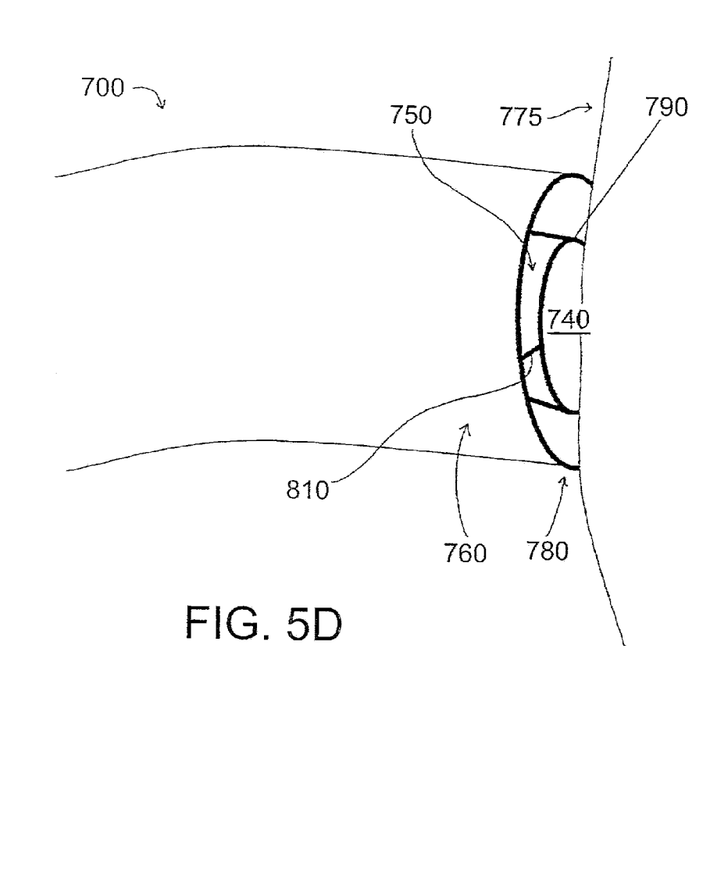
FIG. 5D shows the engagement catheter shown in FIG. 5A approaching a heart wall from inside of the heart.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Figure 6A:
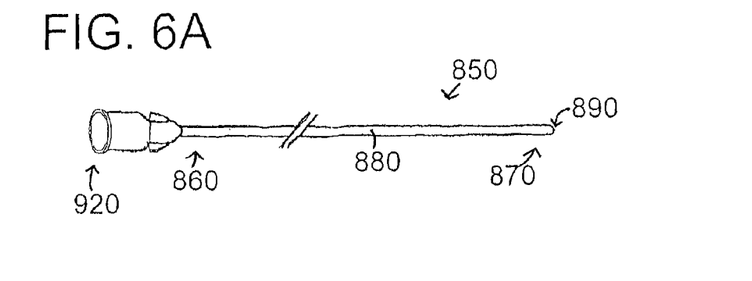
FIG. 6A shows an embodiment of a delivery catheter as disclosed herein.
Figure 6B:
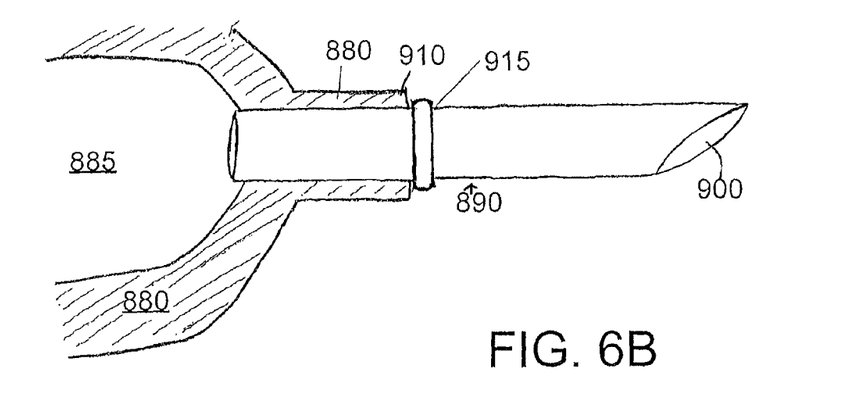
FIG. 6B shows a close-up view of the needle shown in FIG. 6A.
Figure 6C:
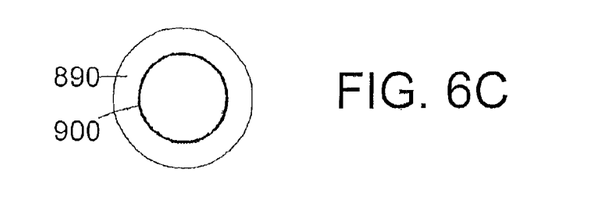
FIG. 6C shows a cross-sectional view of the needle shown in FIGS. 6A and 6B.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tamponade) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrhythmias; (7) to deliver and place epicardial, right atrial, and right and left ventricle pacing leads; (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

While various embodiments of devices for accessing the pericardial space surrounding the heart have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for engaging heart tissue, comprising:
an engagement catheter, comprising:
an elongated tube comprising a proximal end, a distal end, and a single internal lumen extending between the proximal end and the distal end;
a vacuum port in communication with the proximal end of the tube, the vacuum port operatively connected to the single internal lumen and capable of operative connection to a vacuum source; and
a suction port in communication with the single internal lumen at or near the distal end of the tube, the suction port configured to removably engage a targeted tissue on the interior of a wall of a heart, such that the suction port is capable of forming a reversible seal with the wall of the heart when the vacuum source is operatively attached to the vacuum port;
wherein the engagement catheter is configured for percutaneous intravascular insertion into a patient through a blood vessel of the patient and further configured for advancement to the targeted tissue through the blood vessel;
wherein the suction port is configured to removably attach to the targeted tissue under vacuum applied from the vacuum source after introduction of a portion of the engagement catheter into the blood vessel;
wherein the engagement catheter is configured to permit at least a portion of the engagement catheter to be retracted after percutaneous intravascular insertion, while remaining removably attached to the targeted tissue due to vacuum from the vacuum source through the single internal lumen of the engagement catheter and suction engagement from the suction port, so to locally increase a distance between the targeted tissue and a pericardium surrounding the heart; and
a second device, the second device selected from the group consisting of a delivery catheter and a needle; and
wherein the engagement catheter is configured to receive the second device delivered through the vacuum port into the single internal lumen of the engagement catheter and to permit operation of the second device within the single internal lumen while maintaining the reversible seal under vacuum.

2. The engagement catheter of claim 1, wherein when the engagement catheter is used to removably engage the targeted tissue, a delivery catheter may be inserted into and/or removed from the single internal lumen of the engagement catheter.

3. The engagement catheter of claim 1, wherein the suction port is configured to removably engage a portion of an atrial wall, an atrial appendage, a right atrial wall, or a right atrial appendage.

4. The engagement catheter of claim 1, further comprising:
at least one internal lumen support positioned within the single internal lumen and attached to the tube, the at least one internal lumen support extending from the distal end of the tube along at least part of a length of the tube.

5. The engagement catheter of claim 4, wherein the elongated tube comprises a second lumen extending between the proximal end and the distal end.

6. The engagement catheter of claim 1, further comprising:
an injection channel formed along the length of the tube, the injection channel having at its distal end at least one opening for administering a fluid to the targeted tissue, the injection channel capable of operable attachment to an external fluid source at the proximal end of the injection channel, such that fluid from the external fluid source can flow through the injection channel to the targeted tissue when the external fluid source is operatively attached to the injection channel.

7. A system for use with a vacuum source for engaging a tissue, the system comprising:
an engagement catheter comprising:
a single lumen extending between a proximal end and a distal end;
a suction port located at or near the distal end of the engagement catheter and in communication with the single lumen of the engagement catheter, the suction port configured to allow the distal end to removably engage a surface of a bodily tissue; and
a vacuum port located at the proximal end of the engagement catheter, the vacuum port in communication with the single lumen of the engagement catheter and capable of operative connection to a vacuum source;
wherein the engagement catheter is configured for percutaneous intravascular insertion into a patient through a blood vessel and advancement to the surface of the bodily tissue;
wherein when a vacuum source is operatively attached to the vacuum port, the distal end is capable of forming a reversible seal with the surface of the bodily tissue; wherein the engagement catheter is configured to locally increase a distance between the bodily tissue and a second tissue behind the first tissue by retracting the bodily tissue away from the second tissue while the reversible seal is formed; and
a second device, the second device selected from the group consisting of a delivery catheter and a needle; and
wherein the engagement catheter is configured to receive the second device delivered through the vacuum port into the single lumen of the engagement catheter and to permit operation of the second device within the single lumen while maintaining the reversible seal under vacuum.

8. The engagement catheter of claim 7, further comprising:
a second lumen extending between the proximal end and the distal end, the first lumen and the second lumen separated by an inner wall within the engagement catheter and having a concentric axis; and
at least one internal lumen support positioned within the second lumen and attached to the inner wall and an outer wall of the engagement catheter along at least a substantial portion of a longitudinal length of the engagement catheter.

9. The engagement catheter of claim 7, wherein the engagement catheter is configured so that when the engagement catheter is used to form the reversible seal under vacuum through the single lumen using the suction port, a second device can be delivered through the vacuum port into the single lumen of the engagement catheter while maintaining the reversible seal.

10. The engagement catheter of claim 7, wherein the engagement catheter is configured for advancement to a heart through the blood vessel.

11. The engagement catheter of claim 10, wherein the second tissue comprising a pericardium surrounding the heart, and wherein the engagement catheter is capable of locally increasing a pericardial space between the bodily tissue and the pericardium.

12. A system for engaging mammalian tissue, comprising:
an engagement catheter, comprising:
   an elongated tube comprising a proximal end, a distal end, and a single internal lumen extending between the proximal end and the distal end;
   a vacuum port in communication with the proximal end of the tube, the vacuum port operatively connected to the single internal lumen and capable of operative connection to a vacuum source; and
   a suction port in communication with the single internal lumen at or near the distal end of the tube, the suction port configured to removably engage a targeted tissue, such that the suction port is capable of forming a reversible seal with the targeted tissue when the vacuum source is operatively attached to the vacuum port;
   wherein the engagement catheter is configured for percutaneous intravascular insertion into a patient through a blood vessel and advancement to the targeted tissue;
   wherein the suction port is configured to removably attach to the targeted tissue under vacuum applied from the vacuum source after introduction of a portion of the engagement catheter into the blood vessel; wherein the engagement catheter is configured to permit at least a portion of the engagement catheter to be retracted after percutaneous intravascular insertion, while remaining removably attached to the targeted tissue due to vacuum from the vacuum source through the single internal lumen of the engagement catheter and suction engagement from the suction port, so to locally increase a distance between the targeted tissue and a second tissue behind the bodily tissue; and
   a second device, the second device selected from the group consisting of a delivery catheter and a needle; and
   wherein the engagement catheter is configured to receive the second device delivered through the vacuum port into the single internal lumen of the engagement catheter and permit operation of the second device within the single internal lumen while maintaining the reversible seal under vacuum.

13. The engagement catheter of claim 12, wherein when the engagement catheter is used to removably engage the targeted tissue, a delivery catheter may be inserted into and/or removed from the single internal lumen of the engagement catheter.

14. The engagement catheter of claim 12, wherein the suction port is configured to removably engage a portion of an atrial wall, an atrial appendage, a right atrial wall, or a right atrial appendage.

15. The engagement catheter of claim 12, further comprising:
   at least one internal lumen support positioned within the single internal lumen and attached to the tube, the at least one internal lumen support extending from the distal end of the tube along at least part of a length of the tube.

16. The engagement catheter of claim 15, wherein the elongated tube comprises a second lumen extending between the proximal end and the distal end.

17. The engagement catheter of claim 12, further comprising:
   an injection channel formed along the length of the tube, the injection channel having at its distal end at least one opening for administering a fluid to the targeted tissue, the injection channel capable of operable attachment to an external fluid source at the proximal end of the injection channel, such that fluid from the external fluid source can flow through the injection channel to the targeted tissue when the external fluid source is operatively attached to the injection channel.

18. The engagement catheter of claim 12, wherein the engagement catheter is configured for advancement to a heart through the blood vessel.

* * * * *